(12) United States Patent
Victor

(10) Patent No.: US 7,556,777 B2
(45) Date of Patent: Jul. 7, 2009

(54) SPECIMEN VIAL CAP HANDLER AND SLIDE LABELER

(75) Inventor: Richard Victor, Mendon, MA (US)

(73) Assignee: Cytyc Corporation, Marlborough, MA (US)

( * ) Notice: Subject to any disclaimer, the term of this patent is extended or adjusted under 35 U.S.C. 154(b) by 513 days.

(21) Appl. No.: 11/076,352

(22) Filed: Mar. 8, 2005

(65) Prior Publication Data

US 2006/0210432 A1   Sep. 21, 2006

(51) Int. Cl.
    *B01L 11/00*   (2006.01)
(52) U.S. Cl. .................. 422/101; 422/63; 422/68.1; 436/46; 436/63; 436/174; 436/177; 436/178
(58) Field of Classification Search ............. 422/63–67, 422/68.1, 101; 436/46–49, 63, 64, 174–178
See application file for complete search history.

(56) References Cited

U.S. PATENT DOCUMENTS

| | | | |
|---|---|---|---|
| 4,753,358 A | 6/1988 | Virca et al. |
| 4,917,867 A | 4/1990 | Jensen et al. |
| 5,064,059 A | 11/1991 | Ziegler et al. |
| 5,143,627 A | 9/1992 | Lapidus et al. |
| 5,341,854 A | 8/1994 | Zezulka et al. |
| 5,364,597 A | 11/1994 | Polk, Jr. et al. |
| 5,479,969 A | 1/1996 | Hardie et al. |
| 5,772,818 A | 6/1998 | Polk, Jr. et al. |
| 5,852,590 A | 12/1998 | de la Huerga |
| 5,866,690 A | 2/1999 | Bogoch |
| 5,873,857 A | 2/1999 | Kriesel |
| 5,907,493 A | 5/1999 | Boyer et al. |
| 5,946,883 A | 9/1999 | Yuyama et al. |
| 6,015,064 A | 1/2000 | Liu |
| 6,066,300 A | 5/2000 | Carey et al. |
| 6,096,562 A | 8/2000 | Bunn et al. |
| 6,115,996 A | 9/2000 | Yuyama et al. |
| 6,225,125 B1 | 5/2001 | Lapidus |
| 6,258,041 B1 | 7/2001 | Pitesky |
| 6,259,654 B1 | 7/2001 | de la Huerga |
| 6,293,387 B1 | 9/2001 | Forster |
| 6,308,494 B1 | 10/2001 | Yuyama et al. |
| 6,318,190 B1 | 11/2001 | Radcliffe et al. |
| 6,319,668 B1 | 11/2001 | Nova et al. |

(Continued)

FOREIGN PATENT DOCUMENTS

WO      WO 01/67066 A2    9/2001

OTHER PUBLICATIONS

PCT International Search Report for PCT/US2006/007789, Applicant: Cytyc Corporation, Form PCT/USA/210, dated Jul. 6, 2006 (4 pages).

(Continued)

*Primary Examiner*—Jill Warden
*Assistant Examiner*—Dwayne K Handy
(74) *Attorney, Agent, or Firm*—Vista IP Law Group LLP

(57) ABSTRACT

A composite modular system for handling biological sample vials and slides comprises a vial scanner configured to read indicia on the sample vials, a slide labeler configured to mark the slides, a cap manipulator configured to uncap and cap the vials, and a controller, where all other elements are in communication with the controller and the system outputs the uncapped vial and the marked slide.

18 Claims, 5 Drawing Sheets

U.S. PATENT DOCUMENTS

| | | | |
|---|---|---|---|
| 6,343,690 B1 | 2/2002 | Britton et al. | |
| 6,383,820 B1 | 5/2002 | Bunn et al. | |
| 6,385,943 B2 | 5/2002 | Yuyama et al. | |
| 6,488,650 B1 | 12/2002 | Epstein et al. | |
| 6,495,106 B1 | 12/2002 | Kalra et al. | |
| 6,529,446 B1 | 3/2003 | de la Huerga | |
| 6,562,299 B1 | 5/2003 | Ostgaard et al. | |
| 6,572,824 B1 | 6/2003 | Ostgaard et al. | |
| 6,634,244 B2 | 10/2003 | Radcliffe et al. | |
| 7,125,523 B2 * | 10/2006 | Sillman | 422/104 |
| 2003/0090959 A1 | 5/2003 | Mayer | |
| 2003/0092186 A1 * | 5/2003 | Pressman et al. | 436/46 |
| 2003/0207456 A1 | 11/2003 | Ostgaard et al. | |
| 2003/0214388 A1 * | 11/2003 | Stuart et al. | 340/10.1 |
| 2003/0231986 A1 * | 12/2003 | Kocher | 422/99 |
| 2005/0051614 A1 * | 3/2005 | Albany | 235/375 |
| 2005/0159982 A1 * | 7/2005 | Showalter et al. | 705/2 |
| 2005/0242963 A1 * | 11/2005 | Oldham et al. | 340/572.8 |
| 2005/0276728 A1 * | 12/2005 | Muller-Cohn et al. | 422/102 |
| 2006/0239867 A1 * | 10/2006 | Schaeffer | 422/102 |

OTHER PUBLICATIONS

PCT Written Opinion of the International Searching Authority for PCT/US2006/007789, Applicant: Cytyc Corporation, Form PCT/USA/237) dated Jul. 6, 2006 (4 pages).

* cited by examiner

US 7,556,777 B2

SPECIMEN VIAL CAP HANDLER AND SLIDE LABELER

FIELD OF INVENTION

The present invention generally relates to systems for storing biological specimens, and more particularly, to systems and methods for automatically removing caps from biological sample vials and for labeling biological sample slides.

DESCRIPTION OF RELATED ART

Many medical diagnostic tests, such as pap smears, require a physician to collect cells by brushing and/or scraping a skin or mucous membrane in a target area with an instrument. The collected cells are typically smeared ("fixed") onto a slide, and stained to facilitate examination under a microscope by a cytotechnologist and/or pathologist. For example, a pathologist may employ a polychrome technique, characterized by staining the nuclear part of the cells, to determine the presence of dysplasia or neoplasia. The pathologist may also apply a counter-stain for viewing the cytoplasm of the cells. Because the sample may contain debris, blood, mucus, and other obscuring artifacts, the test may be difficult to evaluate, and may not provide an accurate diagnostic assessment of the collected sample.

Cytology based on the collection of the exfoliated cells into a liquid preservative offers many advantages over the traditional method of smearing the cells directly onto the slide. A slide can be prepared from the cell suspension using a filter transfer technique, as disclosed in U.S. Pat. Nos. 6,572,824, 6,318,190, 5,772,818, 5,364,597, and 5,143,627, which are expressly incorporated herein by reference.

Filter transfer methods generally start with a collection of cells suspended in a liquid. These cells may be collected and dispersed into a liquid preservative or they may naturally exist in a collected biological liquid. Dispersion in liquid preservatives containing methanol, such as PreservCyt™ solution, breaks up mucus and lyses red blood cells and inflammatory cells, without affecting the cells of interest. The liquid is passed through a filter with a fixed diameter aperture covered by a membrane to concentrate and collect the cells. Debris, such as lysed blood cells and dispersed mucus, which flow through the pores of the membrane, are not collected on the membrane and are greatly reduced by the combined method of dispersion and filtering. Then the cells collected on the membrane are transferred onto a slide.

Existing filter transfer methods include the steps of manually removing caps from and reattaching caps to specimen ("sample") vials, reading the indicia on the sample vials; manually labeling slides with indicia corresponding to that on the sample vials, and manually recording the correlation between samples and slides. These tasks are repetitious and time consuming. In addition to taking up valuable laboratory technician time, manually processing large numbers of samples can potentially lead to errors because of human involvement in the labeling of slides, recording the correlation between sample vials and slides, and the reattaching caps to processed sample vials. Such errors could include reattaching the wrong caps to sample vials, mislabeling slides, and associating samples with the wrong slides. Reattaching the wrong caps to sample vials may lead to contamination of samples.

Contamination has at least two consequences. First, some biological samples are very inconvenient, if not impossible, to re-harvest. While it is highly inconvenient for a patient to repeat a pap smear, it is may not be possible to repeat a biopsy on a mole that has been removed to test for malignancy. Second, for those situations where a second sample collection is not a viable option, chain of custody issues can have serious repercussions. These chain of custody concerns apply equally to mislabeling and correlation errors. Such chain of custody issues can call into doubt entire batches of test results and, in the worst cases, all results from a clinical lab.

Fully automated batch processing filter transfer systems exist, but these systems may not be economically feasible for all laboratories. Therefore, the price of fully automated systems forces many laboratories to assume the costs and risks of manually processing sample vials and sample slides.

SUMMARY OF THE INVENTION

In one embodiment, a composite modular system for handling biological sample vials and slides comprises a vial scanner configured to read indicia on biological sample vials, a slide labeler configured to mark biological sample slides, a cap manipulator configured to remove and reattach caps on the sample vials, and a controller, where the vial scanner, slide labeler and cap manipulator are in communication with the controller and the system is configured to receive capped sample vials and unlabeled slides, and to output respective uncapped sample vials and associated labeled slides. The vial reader may comprise a bar code scanner. The slide labeler may comprise an ink printer or an applicator, which may attach a pre-printed label or an identifying integrated circuit chip to the slide. The integrated circuit chip may already be attached to the slide and the slide labeler may burn identifying data onto the chip.

In various embodiments, the slide labeler is configured to mark the sample slides with a bar code, an alphanumeric character, or an electromagnetic signal. In various embodiments, the cap manipulator rotates either a vial relative to a cap or a cap relative to a vial.

In one embodiment, the controller comprises a translator, which converts between bar codes and alphanumeric characters. The controller may further comprise a cap tracker in communication with the cap manipulator, where the cap tracker assigns identifiers, which may be a virtual identifier, to the vial caps and the assigned identifiers correspond to vial indicia on a vial associated with the respective cap. In various embodiments, the cap manipulator is configured to reattach caps to the respective vials from which the caps were removed.

In one embodiment, the composite modular system further comprises a slide reader in communication with the controller, where the slide reader is configured to scan and identify slide indicia on the sample slides, and the controller determines whether the identified slide indicia correspond to vial indicia on a vial associated with the respective slide. The slide reader may comprise an optical character recognition system.

In accordance with another aspect of the invention, a method of handling biological sample vials and slides is provided, the method comprising, in a first embodiment, providing a biological sample vial having an attached cap and vial indicia disposed thereon, automatically reading the vial indicia, providing a biological sample slide, automatically labeling the slide with slide indicia corresponding to the vial indicia, automatically removing the cap from the vial, automatically presenting the uncapped vial and marked slide for further processing. In an alternative embodiment, the cap is automatically reattached to the vial.

In one embodiment, the method of handling biological sample vials and slides further comprises automatically identifying the slide indicia and automatically determining whether the slide indicia corresponds to the vial indicia. In another embodiment, the method further comprises assigning an identifier to the vial cap, the identifier corresponding to vial indicia on the vial.

BRIEF DESCRIPTION OF THE DRAWINGS

In order to better understand and appreciate the invention, reference should be made to the drawings and accompany detailed description, which illustrate and describe exemplary embodiments thereof. For ease in illustration and understanding, similar elements in the different illustrated embodiments are referred to by common reference numerals. In particular.

DETAILED DESCRIPTION OF THE ILLUSTRATED EMBODIMENTS

In the following description of the illustrated embodiments, it will be understood by those skilled in the art that the drawings and specific components thereof are not necessarily to scale, and that various structural changes may be made without departing from the scope or nature of the various embodiments.

Figure 1:
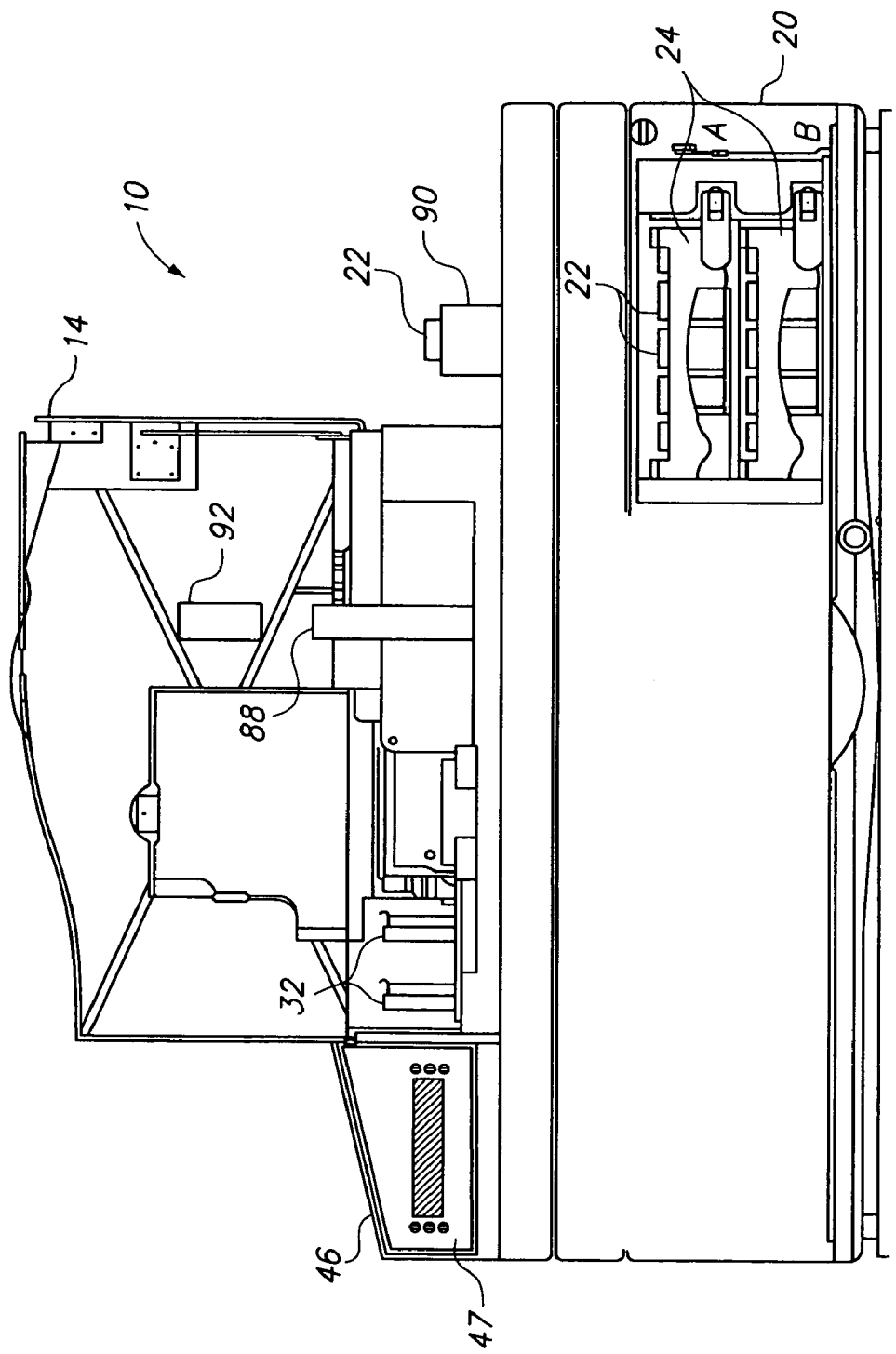
FIG. 1 is a front view of an exemplary composite modular system for removing caps from and reattaching caps to biological sample vials and marking slides according to one embodiment of the invention.
Figure 2:
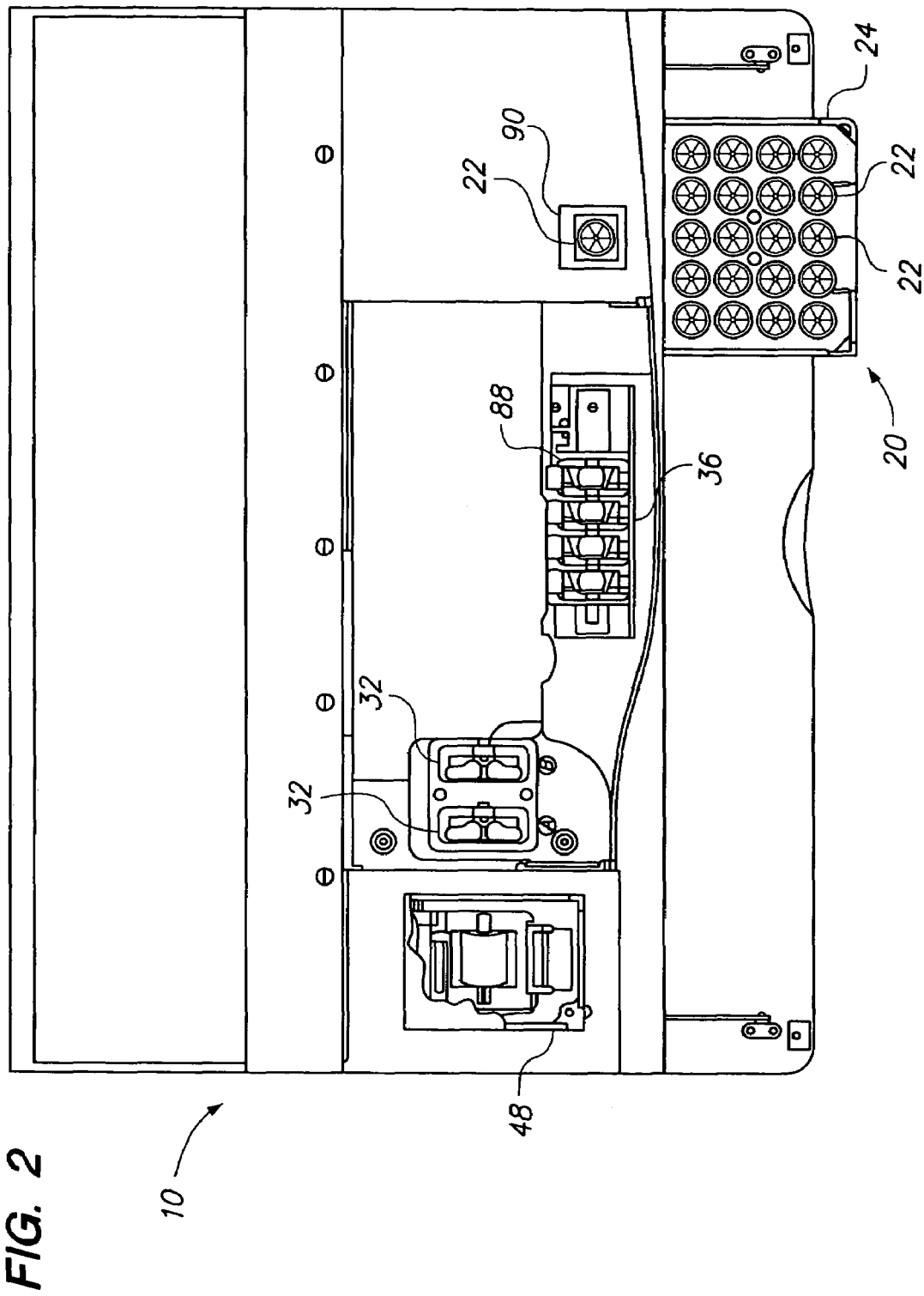
FIG. 2 is a top view of the composite modular system of FIG. 1 with the lid cut away.

Referring to FIGS. 1 and 2, a composite modular system 10 is shown. In this embodiment, the composite modular system 10 accepts trays 24 of capped sample vials 22 and packs of microscope slides 62. The system 10 uncaps a sample vial 22, reads the indicia 58 on the vial 22, marks a slide 62 with corresponding indicia 82, verifies the slide indicia 82, presents the uncapped sample vials 22 and marked slides 62 for further processing, and recaps sample vials 22. Before processing of the sample, the output of the system 10 include both uncapped sample vials 22 and correspondingly marked slides 62 ready for processing. After processing of the sample, the output of the system 10 is recapped sample vials 22 in their original positions in vial trays 24.

Figure 5:
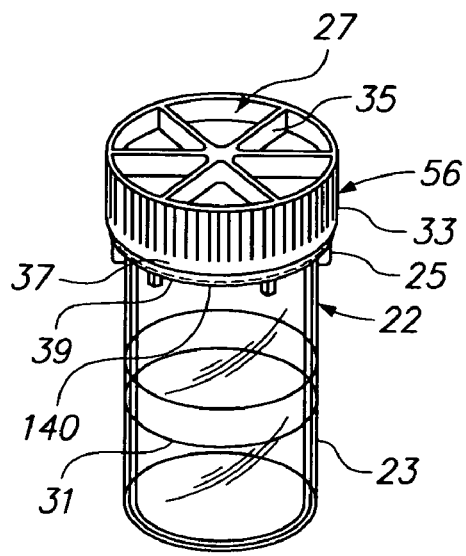
FIG. 5 is a perspective view of a capped sample vial for use with the composite modular system of FIG. 1.

The system 10 includes a loading station 20 for receiving a plurality of patient samples, each disposed in a sample vial 22. The sample vials 22 are best seen in FIG. 5. As depicted, the sample vial loading station 20 may have more than one tier to accommodate multiple sample vial trays 24, two trays 24 being shown. Each tray 24 is removable to facilitate handling and preloading of the vials 22. In one embodiment, each tray 24 may include locations for forty samples vials 22, providing a system 10 that can automatically uncap up to eighty sample vials 22 and label up to eighty blank glass microscope slides 62 before needing to be reloaded.

The microscope slides 62 are preloaded in two removable cartridges 32, each with the capacity to hold one hundred slides 62. Two cartridges 32 are provided to ensure that there are a sufficient number of slides 62 available in the system 10 to process the maximum number of sample vials 22. While glass microscope slides 62 are typically used for preparing cytological specimens, other analytical elements, such as natural or synthetic material assay strips and the like, are suitable for other analyses and testing, as known by those skilled in the art, and could be employed in the system 10 with suitable handling equipment.

Alternatively, a sample vial 22 and a slide 62 may be manually loaded into a similar system. Such an alternative system would not include a loading station or slide cartridges.

A computer controller or processor 46 is provided to communicate with and coordinate operation of the various sensors and components of the system 10 to permit automatic operation during vial uncapping, slide labeling and vial recapping. The processor 46 includes an appropriate operator interface 47 with associated input keypad or buttons and an output display, such as a liquid crystal diode display. Instructions, prompts, and error messages may be in text, error code, or symbol formats. Text displays may be in a variety of operator selectable languages, such as English, French, German, Italian, Japanese, and Spanish. Audible outputs corresponding to operator prompts, error conditions, keypad inputs, and completion of automatic processing may be provided. A thermal paper printer 48 or other type of printer may be provided, as well, to generate a permanent paper record of system operation and sample processing. For example, for each batch of eighty or fewer sample vials 22 processed, the printer 48 may generate a report containing the date and time processing began, a listing of the sample vials 22 not successfully processed (including error type and tray location), a listing of the sample vials 22 successfully processed (including sample identification information and tray location), and a listing of the correlation between sample vials 22 and slides 62. Such a correlation list may include human readable characters identifying the patient, the date the sample was collected, the sample vial and the slide.

Figure 3:
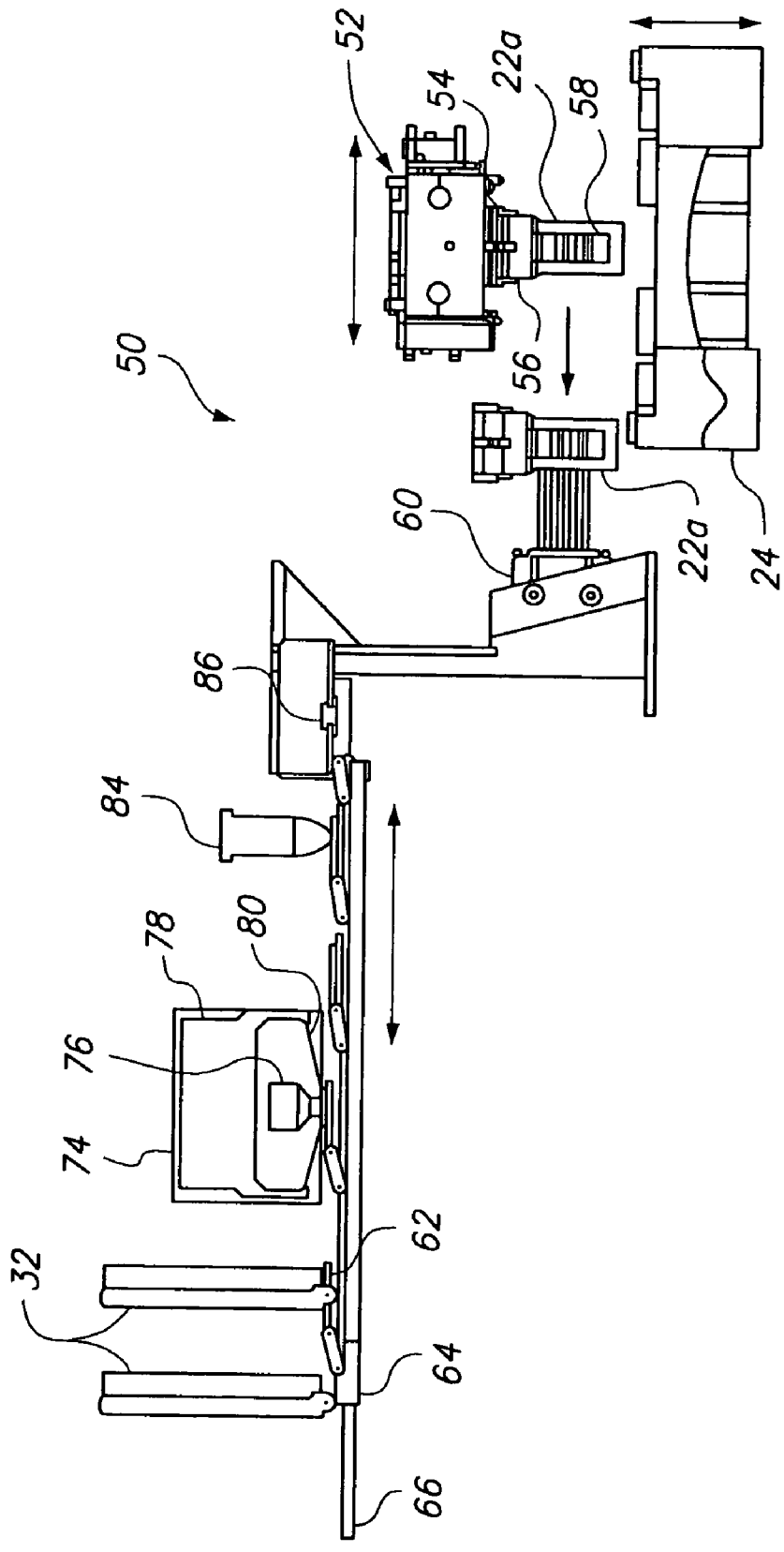
FIG. 3 is a schematic front view of an identification correlation subsystem of the composite modular system of FIG. 1.
Figure 4:
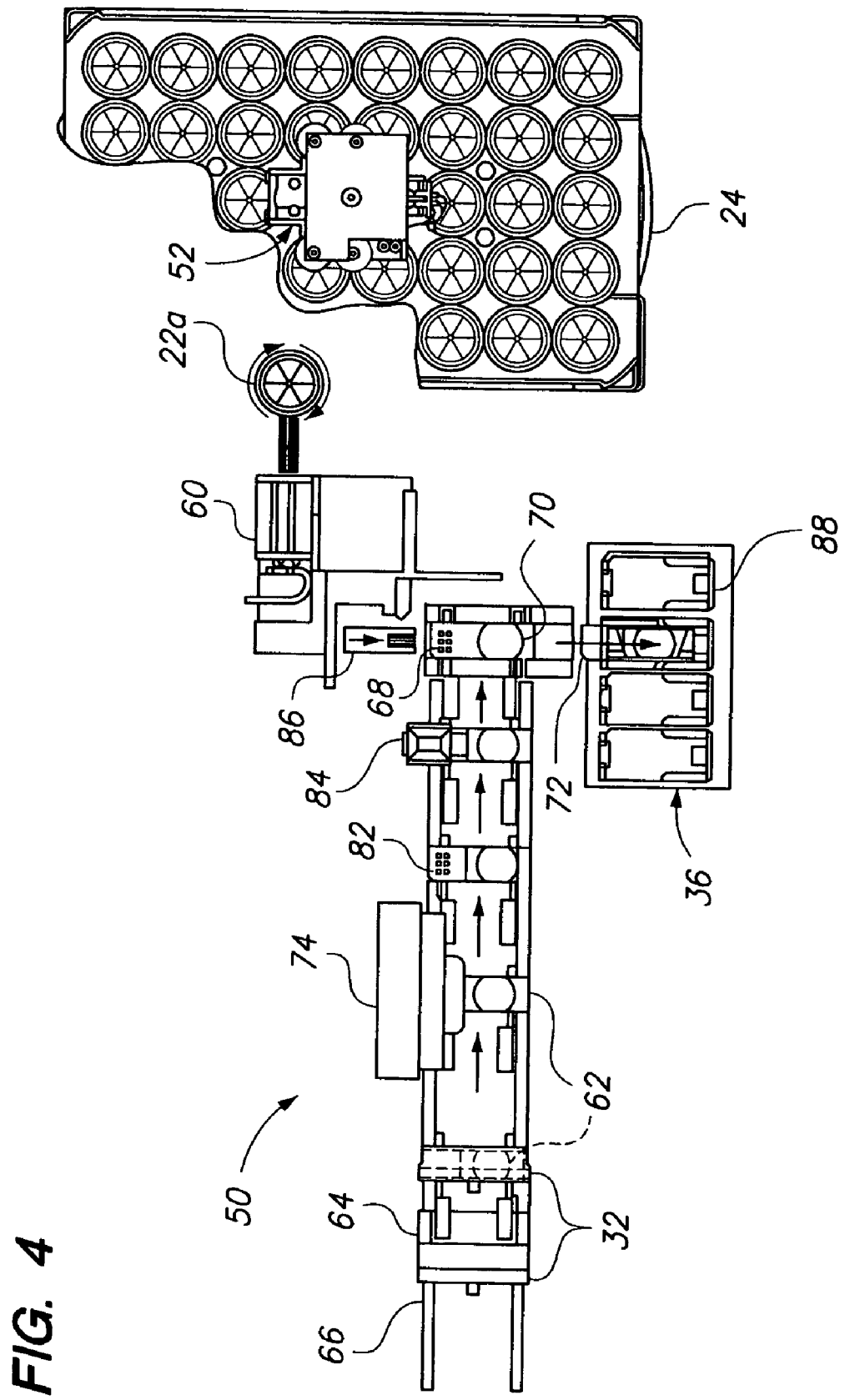
FIG. 4 is a schematic top view of the identification correlation subsystem of FIG. 3.

In order that the system 10 maintains correlation between each sample vial 22 and a respective slide 62, an identification correlation subsystem 50 is provided, as depicted schematically in front and top views in FIGS. 3 and 4, respectively. In accordance with one embodiment, in order to prepare a sample vial 22 and a slide 62 for further processing, a selected capped vial 22a is removed from one of the sample vial trays 24 by a sample vial transfer assembly 52. The vial transfer assembly 52 includes a four-fingered gripper 54 configured to reliably and repeatable grasp a cap 56 of the vial 22a. The vial transfer assembly 52 is movable about a plane above the vial tray 24, left to right and into and out of the drawing as depicted in FIG. 3, so that the gripper 54 can be aligned above any of the forty vials 22 loaded in the tray 24. Once aligned with a desired vial 22a, the tray 24 is raised by the tray elevator, the vial cap 56 grasped by the gripper 54 and tightened as will be discussed in greater detail hereinbelow, and the tray 24 lowered. In order to access vials 22 on the other tray 24, the vial transfer assembly 52 can be retracted to one side, outside a footprint of the trays 24 and the tray elevator operated to raise or lower the tray 24, as necessary.

Each vial 22 includes identifying indicia, such as a bar code label 58 mounted thereon, which corresponds to and uniquely identifies the vial 22 and the sample contained therein. The selected vial 22a is then presented by the vial transfer assembly 52 to an identifier, such as a laser scanner bar code reader 60, so that the particular vial 22a can be identified. Because the circumferential orientation of the vials 22 in each tray 24 and that of the respective bar code labels 58 can vary, upon presentation to the bar code reader 60, the vial transfer assembly 52 rotates the sample vial 22a about a vertical axis passing generally through an axial centerline thereof, as best seen in FIG. 4, to present the label 58 to the reader 60.

Once the bar code label 58 or other identifying indicia has been identified and communicated to the processor 46, the processor 46 directs the preparation of an analytical element, such as a microscope slide 62, for further processing with the selected vial 22a.

Referring to FIG. 4, a slide carriage 64, translatable along a carriage rail 66, first extracts a slide 62 from one of the slide cartridges 32. Each slide 62 has tightly toleranced dimensions and chamfered edges to facilitate handling and transfer of the slide 62 by the components of the system 10 and minimize the likelihood of mishandling or jamming. In one embodiment, the slide 62 is manufactured from glass and has a width of about one inch, a length of about three inches, and a thickness of about 0.04 inches. One end 68 of the slide 62 is frosted or coated to facilitate marking, as will be discussed in greater detail hereinbelow. The frosted end 68 may have an area of about one square inch. A frosted annulus 70, defining an area to where the cells are transferred, may also be provided to facilitate manual or automatic scanning of sparse specimens. Additionally, one corner 72 of the frosted end 68 of each slide 62 may be chamfered to a greater degree than the other corners to ensure proper orientation of the slide 62 in the slide cartridge 32 and proper presentation of the slide 62.

Once the bar code label 58 on the sample vial 22a has been identified and before the sample vial 22a is uncapped, the slide carriage 64 conveys the slide 62 to a marker in communication with the processor 46 for marking the slide 62 with indicia corresponding to the sample indicia on the bar code label 58. In one embodiment, the marker may be a printer 74, such as an ink jet printer, thermal printer, laser printer, or other suitable marker capable of producing substantially permanent indicia on the slide 62. In the depicted embodiment, the printer 74 is a dot matrix impact printer utilizing a multi-pin impact head 76 and replaceable ribbon cartridge 78, which feeds an ink ribbon 80 to a zone between the impact head 76 and the slide 62.

The processor 46 next directs the printer 74 to mark the slide 62. The slide indicia may have any of a variety of forms including one or more alphanumeric characters, as shown generally at 82. It is generally desirable to mark the slides 62 with man-readable indicia so that the cytologist examining a slide 62 can readily identify associated sample vial 22. Further, slides 62 with fixed and stained specimens are often archived and retained for extended periods. Accordingly, it is generally desirable to avoid using an indicia standard that may fall into disuse or become obsolete. Because such slides 62 are often archived in slide file drawers, it is generally desirable that the slide indicia 82 be oriented along the width or narrow dimension of the frosted end 68 so as to be readable without requiring removal of the slide 62 from the file drawer.

The slide indicia printing method and printing media should be resistant to the solvents used in the specimen preparing, fixing, and staining processes. Typical solvents include ethanol, methanol, xylene, water, and a clarifier solution consisting of 0.025% glacial acetic acid in distilled water. In general, commercially available carbon black based printing ink ribbons 80 have been found to perform well when printing on frosted ends 68 produced by coating the ends of the slides 62 with a white epoxy paint material.

In order to generate readily discernible characters 82 using a low cost printer 74, the processor 46 may control operation of the printer 74 and the slide carriage 64 so as to first transfer a spot of ink to a first location on the slide 62 and then transfer another spot of ink to a second location offset spatially and slightly overlapping the first location. By double-striking, or alternatively striking a third or more times in different offset directions to blend the ink spots in a particular region of the character, a relatively low cost nine pin dot matrix printer can produce alphanumeric characters substantially visually consistent with those produced by a much more expensive dot matrix printer having many more pins in the impact head.

Alternatively, the slide indicia may also be marked on an adhesive label that is then bonded to the slide 62, such labels and bonding material should be resistant to degradation from subsequent processing such as fixing and staining. The slide 62 may also be electronically "marked" by bonding an integrated circuit chip to the slide 62. The chip emits an unique electromagnetic signal to identify the slide 62.

On the other hand, the integrated circuit chip may already be attached to the slide 62 and the system 10 may burn identifying data onto the chip.

Once the slide 62 is marked, the processor 46 directs the slide carriage 64 to advance the slide 62 along the carriage rail 66 to a reader in communication with the processor 46 for reading the slide indicia 82. In the case where the specimen indicia is composed of alphanumeric characters, the reader may be an optical character recognition (OCR) scanner 84 or system. In one embodiment, a total of four strikes are employed per pin using a nine pin printer in order to meet OCR font specifications typical for higher resolution dot matrix printers.

The processor 46 verifies both that the slide indicia 82 is readable by the OCR scanner 84 and that the slide indicia 82 corresponds to the sample indicia identified from the bar code label 58 on the selected vial 22a. In the event the slide indicia 82 cannot be read or the slide indicia 82 does not correspond to the sample indicia, the slide 62 may be removed automatically from the slide carriage 64 using an ejector or other apparatus, as discussed in greater detail hereinbelow, and discarded in the waste bin 44 or other waste receiving area. If multiple slides 62 fail in succession or if more than a predetermined number of slides fail during processing of a batch of sample vials 22, the system 10 may be programmed optionally to halt automatic operation and alert the operator with a suitable error message.

Upon verification of both criteria, the sample vial transfer assembly 52 removes the cap 56 from the sample vial 22a and moves the sample vial 22a to a vial elevator 90 (see FIGS. 1 and 2) for presentation to a user. The cap 56 is stored inside of the system 10 until the sample vial 22a is returned to the system 10 for recapping. The system 10 assigns a virtual identifier to cap 56 and will only return it to the associated sample vial 22a after the returned vial 22a has been again identified by the bar code reader 60 as described above.

At the same time that the uncapped sample vial 22a is presented to the user, a slide ejector 86 moves the marked slide 62 from the slide carriage 64 to an unloading area 36. Once in the unloading area 36, the marked slide 62 is transported to a slide elevator 88 (see FIGS. 1 and 2) for presentation to a user through an opening 92 in a cover 14 for the system 10. Multiple marked slides 62 are stored in the unloading area 36 so that the system 10 can keep multiple sets of matched sample vials 22 and marked slides 62 ready for the user.

The user may prepare the sample using a filter transfer method, as described above. This filter transfer method may be manual or automated as in Cytyc Corporation's T-2000 system. The sample may also be prepared by either manually or automatically taking an aliquot from the sample. Regardless of the sample preparation method, the system 10 provides an uncapped sample vial 22a and a correspondingly marked slide 62 for use in preparation of the sample. When the sample has been prepared, the user returns the uncapped sample vial 22a to the system 10 for recapping.

After the user returns an uncapped vial 22a to the system 10, the associated cap 56 is replaced on the sample vial 22a and the vial 22a returned to its location in the vial tray 24. If there exist additional sample vials 22 which have not yet been processed, a next vial 22 and an associated next slide 62 are presented to the user.

In order that the system 10 can process automatically uncap and recap the sample vials 22, each vial 22 and cap 56 includes one or more structural features which facilitate grasping of the closed, capped vial 22 by the sample vial transfer assembly 52, as well as removal and reinstallation of the cap 56. In one embodiment depicted in FIG. 5, the sample vial 22 includes a body 23 having a generally cylindrical outer surface, an open end, a closed end, and at least one lug 25 disposed about the outer surface. The lug 25 performs an anti-rotation function, preventing the body 23 from rotating when disposed against adjacent structure. The sample vial cap 56 is releasably engagable with the body 23, the cap 56 including an outer surface with a torque pattern 27 thereon for mating with a rotatable interface of the sample vial transfer assembly 52 as discussed more fully hereinbelow. A seal is disposed between the body 23 and the cap 56 so as to be capable of forming a substantially fluid-tight seal therebetween.

Instead of a single anti-rotation lug 25, the body 23 may include a plurality of lugs 25 disposed about a perimeter of the body 23, such as the six equi-spaced lugs 25 of the embodiment of FIG. 5. While the lugs 25 may be disposed anywhere on the body 23 accessible to the sample vial transfer assembly 52 or related structure of the system 10, the lugs 25 may be disposed advantageously proximate the open end of the body 23 and the cap 56. In this manner, torque may be applied to both the body 23 and the cap 56 at approximately the same axial plane to minimize any induced moment in the vial 22 during removal and installation of the cap 56.

The sample vial body 23 may be manufactured from a substantially transparent or translucent material so that a level of the fluid sample therein can be readily discerned by the system operator to ensure the presence of a sufficient amount of fluid for subsequent processing. The body 23 may also include fluid level indicia 31 disposed on the outer surface thereof, such as a circumferentially-disposed frosted annular band. Accordingly, the vials 22 can be rapidly visually screened by the operator prior to loading in the vial tray 24 to prevent loading a vial 22 with too much or too little fluid which might not be processed successfully. The fluid level indicia 31 may be provided in addition to the sample bar code label 58 discussed hereinabove.

The cap may be manufactured from polypropylene or other suitable material and may include knurling 33 or other anti-slip feature along an outer perimeter thereof to facilitate manual handling by a nurse or doctor during sample procurement, as well as the system operator during manual loading and loading of the sample vial trays 24. The cap torque pattern 27 may be at least one generally radially disposed rib 35. In the embodiment depicted in FIG. 5, the torque pattern 27 includes six generally radially disposed, equi-spaced ribs 35.

The seal may be manufactured from any suitable material which can be sterilized and which is capable of withstanding attack by the preservative fluid, which may typically contain a solution of methanol in a buffer. For example, the seal may be manufactured from a multicomposite material such as a resilient rubber layer laminated with a suitable vapor barrier and may be disposed within the cap 56. The cap 56 and the body 23 may have mating screw threads, a bayonet fitting, or other retention feature so as to be releasably engageable. In one embodiment, a substantially fluid-tight seal between the body 23 and the cap 56 may be formed when at least between about 5 and 50 inch-pounds of torque is applied to the cap 56 relative to the body 23. A more typical torque range may be on the order of about 20 to 30 inch-pounds, with about 25 inch-pounds being preferred. To ensure that the fluid-tight seal is produced when the patient's cells are first disposed in the preservative fluid and to prevent leakage or evaporation of the preservative fluid during transport and storage, the system 10 is programmed to generate approximately 25 inch-pounds of torque during recapping. Further, each of the cap 56 and the body 23 may include alignment markers 37, 39, such that the alignment markers 37, 39 indicate a fluid-tight seal when at least aligned.

Figure 6:
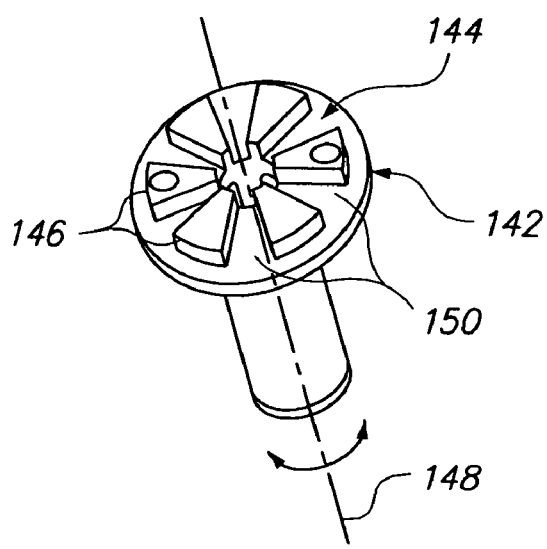
FIG. 6 is a perspective view of a rotatable interface for mating with a torque pattern of the capped sample vial of FIG. 5.

FIG. 6 is a schematic perspective view of one design of a rotatable interface 142 of a cap manipulator disposed radially inwardly of the grippers 54 of the vial transfer assembly 52. The interface 142 includes a torque pattern 144 for mating with the torque pattern 127 of the sample vial cap 56. The rotatable interface 142 is shown inverted, to better depict the interface torque pattern 144 formed therein. In this embodiment, the interface torque pattern 144 includes six raised wedge-shaped sectors 146. The sectors 146 are substantially equi-spaced about the interface 142, which is rotatable about a longitudinal axis 148 thereof, and sized to mate with the torque pattern 127 of the cap 56. Accordingly, the ribs 35 of the cap 56 fit in grooves 150 formed between the sectors 146 of the interface 142 and react against substantially vertical faces of the sectors 146 to permit both loosening and tightening of the cap 56.

Figure 7:
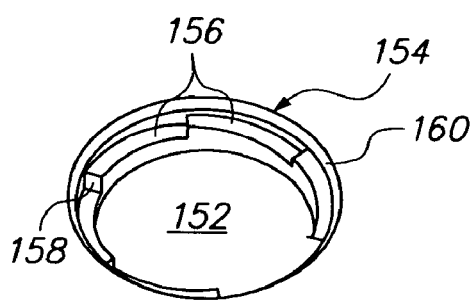
FIG. 7 is a perspective view of a unidirectional interface in a sample vial tray for mating with anti-rotation features of the capped sample vial of FIG. 5.

To prevent rotation of the sample vial body 23 during these operations, the body 23 may be disposed in a bore 152 formed in the sample vial tray 24 having a unidirectional interface 154 along an edge 160 thereof for mating with the lugs 18 of the body 23, as depicted in FIG. 7. The interface 154 includes six ramps 156, each including a substantially vertical face 158 which abuts one of the body lugs 25. Accordingly, the capped vial 22 may be disposed in the bore 152 with a flange 140 of the body 23 supported along the edge 160. The rotatable interface 142 may then be engaged with and tighten the cap 56, to ensure a fluid-tight seal prior to removing the vial 22 from the sample tray 24. Due to the orientation of the ramps 156, the lugs 25 react against the ramp faces 158 during tightening to positively secure and prevent rotation of the vial body 23.

Figure 8:
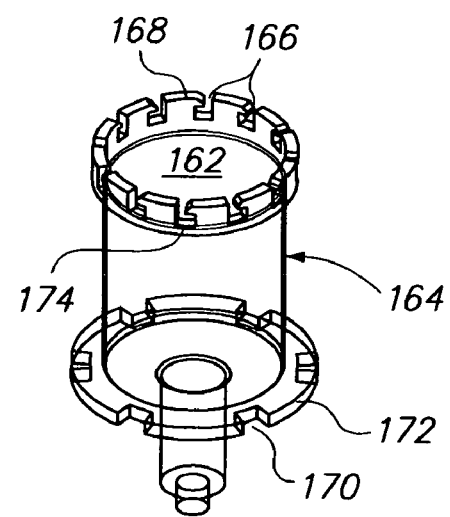
FIG. 8 is a perspective view of a bi-directional interface for mating with anti-rotation features of the capped sample vial of FIG. 5.

Once the cap 56 has been tightened, the vial transfer assembly 52 may grasp the capped vial 22 about the circumference of the cap 56 with the grippers 54, remove the vial 22 from the bore 152 in the tray 24, rotate the vial 22 in front of the bar code reader 60, and deposit the capped vial 22 in a bore 162 formed in a vial sleeve 164, such as that depicted in FIG. 8 in wire form representation. The six lugs 2.5 of the capped vial 22 are received in every other one of twelve axially extending slots 166 formed along an upper edge 168 of the sleeve 164, the flange 140 of the vial 22 being supported by the edge 168. Once in the bore 162 with the lugs 25 disposed in the slots 166, further processing may proceed.

As discussed hereinabove, a slide 62 is printed and the slide indicia 82 verified as being readable and corresponding to the sample vial bar code label 58. The vial 22 may then be uncapped and presented to the user along with a correspondingly marked slide 62. During the uncapping, according to one embodiment, a pin, clamp, or other structural feature of the system 10 may engage one of a series of notches 170 formed in a flange 172 of the sleeve 164 to prevent rotation of the sleeve 164 and the vial 22 disposed therein while the rotatable interface 142 engages and unscrews the cap 56. The cap 56 is then retracted by the gripper 54 of the vial transfer assembly 52 and uncapped vial 22 is presented to the user. Once the uncapped vial 22 has been returned to the system 10, the associated cap 56 is reoriented over the open vial 22 and screwed onto the body 23 until a substantially fluid-tight seal has been formed. The axially extending slots 166 which engage the lugs 25 form a bidirectional interface, to react against the body lugs 25 during both removal and installation of the cap 56 on the body 23. Each of the axial slots 166 may be formed to include, optionally, a generally circumferentially disposed portion, shown generally at 174, to lock a suitably sized lug against axial translation, if desired.

Of course, other suitable materials, dimensions, and configurations for the body 23, the cap 56, the ribs 35, the lugs 25, the fluid level indicia 31, and other features of the sample vial 22 will be apparent to those skilled in the art, those disclosed being provided as examples only. For example, while the mating ribs 35 and sectors 146 provide a positive, self-centering drive, other mating structure such as pins and annular tracks may be used. Further, the sample vial 22 may be used in other applications and contain other than cytological samples in preservative solution.

Although various embodiments of the invention have been shown and described herein, it should be understood that the above description and figures are for purposes of illustration only, and are not intended to be limiting of the invention, which is defined only by the appended claims and their equivalents.

What is claimed:

1. A composite modular system for handling biological sample vials and slides, comprising:
    a vial scanner configured to read indicia on biological sample vials, the indicia corresponding to patient identification information;
    a slide labeler comprising an applicator configured to attach an integrated circuit chip to the biological sample slides, the slide labeler configured to transmit an electronic signal for storage on the integrated circuit chip, the stored information corresponding to patient identification information;
    a cap manipulator configured to remove and reattach caps on the sample vials; and
    a controller, wherein the vial scanner, slide labeler and cap manipulator are in communication with the controller, and
    wherein the system is configured to receive capped sample vials and unlabeled slides, and to output respective uncapped sample vials and associated slides having attached thereto an integrated circuit chip configured to emit a unique electromagnetic signal that corresponds to the patient identification information of the sample vial indicia.

2. The system of claim 1, wherein the vial scanner comprises a bar code scanner.

3. The system of claim 1, wherein the slide labeler comprises an integrated circuit chip data burner.

4. The system of claim 1, wherein the applicator is configured to attach respective pre-printed labels to the sample slides.

5. The system of claim 1, wherein the slide labeler is configured to mark the sample slide with respective electromagnetic signal sources.

6. The system of claim 1, wherein the cap manipulator is configured to rotate a vial relative to a cap.

7. The system of claim 1, wherein the cap manipulator is configured to rotate a cap relative to a vial.

8. The system of claim 1, wherein the controller comprises a translator for converting between bar codes and alphanumeric characters.

9. The system of claim 1, wherein the controller comprises a cap tracker in communication with the cap manipulator, wherein the cap tracker assigns identifiers to the vial caps, the assigned identifiers corresponding to vial indicia on a vial associated with the respective cap.

10. The system of claim 9, wherein the identifier is a virtual identifier.

11. The system of claim 1, wherein the cap manipulator is configured to reattach caps to the respective vials from which the caps were removed.

12. The system of claim 1, further comprising a slide reader in communication with the controller, wherein the slide reader reads the electromagnetic signal that corresponds to the stored patient identification information, and the controller determines whether the stored patient identification information corresponds to patient identification information contained in the vial indicia on a vial associated with the respective slide.

13. A method of handling biological sample vials and slides, comprising:
    providing a biological sample vial having an attached a cap and vial indicia disposed thereon, the indicia corresponding to patient identification data;
    automatically reading the vial indicia;
    providing a biological sample slide;
    automatically attaching an integrated circuit chip to the slide, the integrated circuit chip being configured to store patient identification data identifying the biological sample slide;
    automatically removing the cap from the vial;
    automatically presenting the uncapped vial and marked slide for further processing.

14. The method of claim 13, further comprising automatically reattaching the cap to the vial.

15. The method of claim 13, further comprising
    reading an electromagnetic signal sent from the integrated circuit chip; and
    automatically determining whether the patient identification data stored in the integrated circuit chip on the slide corresponds to the patient identification data on the vial indicia.

16. The method of claim 13, further comprising assigning an identifier to the vial cap, the identifier corresponding to vial indicia on the vial.

17. A method of handling biological sample vials and slides, comprising:
    providing a biological sample vial having an attached a cap and vial indicia disposed thereon, the indicia corresponding to patient identification information;
    automatically reading the vial indicia;
    providing a slide having attached thereto an integrated circuit chip configured to store patient identification information
    reading an electromagnetic signal emitted from the integrated circuit chip on the slide and verifying that the patient identification information of the slide corresponds to the patient identification information contained in the vial indicia; and
    automatically removing the cap from the vial if the patient identification information of the slide corresponds to the patient identification information contained in the vial indicia and automatically presenting the uncapped vial and marked slide for further processing.

18. The method of claim 17, wherein the integrated circuit chip is attached to the slide using a labeler.

* * * * *